US010167515B2

(12) United States Patent
Park et al.

(10) Patent No.: US 10,167,515 B2
(45) Date of Patent: Jan. 1, 2019

(54) MOLECULAR ANALYSIS USING A MAGNETIC SIFTER AND NANOWELL SYSTEM

(71) Applicant: The Board of Trustees of the Leland Stanford Junior University, Palo Alto, CA (US)

(72) Inventors: Seung-min Park, Menlo Park, CA (US); Dawson Wong, San Jose, CA (US); Chin Chun Ooi, Menlo Park, CA (US); Sanjiv Sam Gambhir, Portola Valley, CA (US); Viswam S. Nair, Menlo Park, CA (US); Shan X. Wang, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 224 days.

(21) Appl. No.: 15/133,996

(22) Filed: Apr. 20, 2016

(65) Prior Publication Data
US 2016/0230237 A1 Aug. 11, 2016
US 2018/0002760 A2 Jan. 4, 2018

Related U.S. Application Data

(60) Provisional application No. 62/149,978, filed on Apr. 20, 2015, provisional application No. 62/150,100, filed on Apr. 20, 2015.

(51) Int. Cl.
*C12Q 1/6886* (2018.01)
*C12Q 1/686* (2018.01)
*G06F 17/30* (2006.01)

(52) U.S. Cl.
CPC .......... *C12Q 1/6886* (2013.01); *C12Q 1/686* (2013.01); *G06F 17/30132* (2013.01); *C12Q 2600/158* (2013.01)

(58) Field of Classification Search
CPC ............ C12Q 1/6886; C12Q 2600/156; C12Q 2600/158
See application file for complete search history.

(56) References Cited

U.S. PATENT DOCUMENTS

| 7,615,382 B2 | 11/2009 | Wang | |
| 2008/0176290 A1* | 7/2008 | Joseph | G01N 21/253 435/91.2 |

OTHER PUBLICATIONS

Park, S. et al. Proceedings of the 106th Annual Meeting of the AACR, Apr. 18-22, 2015, Abstract LB-280 (Apr. 18, 2015).*
(Continued)

*Primary Examiner* — Diana B Johannsen
(74) *Attorney, Agent, or Firm* — Lumen Patent Firm (57) ABSTRACT

A method for identification of circulating tumor cells (CTCs) in a blood sample uses magnetic enrichment and a nanowell assay. The CTCs are magnetically labeled with cancer cell markers conjugated to magnetic nanoparticles and then separated by passing the blood sample through a magnetic sifter. The enriched CTCs are then loaded into a microfluidic single-cell molecular assay comprising an array of 25,600 or more nanowells, each containing at most a single one of the CTCs. Using multiple fluorescent gene markers, simultaneous multiple-color multiplexed gene expression of the CTCs is performed, preferably using RT-PCR. Images of fluorescence signals from individual nanowells are analyzed to identify CTCs.

7 Claims, 5 Drawing Sheets

(56) References Cited

OTHER PUBLICATIONS

Park, s. et al. World Molecular Imaging Congress 2014, Abstract SS 122 (Sep. 2014).*
AACR Annual Meeting 2015, "Technology at the Annual Meeting", 3 pages, Apr. 2015.*
Earhart, C.M. et al. Lab Chip 14:78 (Jan. 2014; online Jul. 23, 2013).*
Harouaka, R. et al. Pharmacology & Therapeutics 141:209 (Feb. 2014).*
Su et al., "Composite Organic-Inorganic Nanoparticles (COINs) with Chemically Encoded Optical Signatures," Nano Letters, vol. 5, No. 1, 2005, p. 49-54.
Andreopoulou et al. "Comparison of assay methods for detection of circulating tumor cells in metastatic breast cancer," International Journal of Cancer vol. 130, Issue 7, pp. 1590-1597, Apr. 1, 2012.
Tong et al., "Application of immunomagnetic cell enrichment in combination with RT-PCR for the detection of rare circulating head and neck tumor cells," Cytometry Part B: Clinical Cytometry, vol. 72B, Issue 5, p. 310-323, Sep. 2007.
Zborowski et al. "Rare Cell Separation and Analysis by Magnetic Sorting," Anal Chem. Nov. 1, 2011; 83(21): 8050-8056.
Chen et al., "Rare cell isolation and analysis in microfluidics," Lab Chip, 2014, vol. 14, 626.

\* cited by examiner

*Fig. 4C* HCC827 – Mutant

*Fig. 4D* H661 – Wild-type

*Fig. 5*

MOLECULAR ANALYSIS USING A MAGNETIC SIFTER AND NANOWELL SYSTEM

CROSS-REFERENCE TO RELATED APPLICATIONS

This application claims priority from U.S. Provisional Patent Application 62/149,978 filed Apr. 20, 2015, and from U.S. Provisional Patent Application 62/150,100 filed Apr. 20, 2015, both of which are incorporated herein by reference.

STATEMENT OF GOVERNMENT SPONSORED SUPPORT

This invention was made with Government support under contract CA151459 and CA185804 awarded by the National Institutes of Health. The Government has certain rights in the invention.

FIELD OF THE INVENTION

The present invention relates generally to biomedical sensing techniques. More particularly, the invention relates to systems and methods for identifying and classifying circulating tumor cells.

BACKGROUND OF THE INVENTION

Circulating tumor cells (CTCs), shed from a primary tumor into the bloodstream, may be valuable diagnostic/prognostic biomarkers that contain actionable genetic information for tumor analysis. Unfortunately, the rarity of CTCs in comparison to other blood components necessitates high-throughput separation technologies for efficient enrichment and elaborate downstream analysis. Moreover, genetic data extraction from CTCs currently suffers from a lack of reliable analytical methods capable of handling a low number of cells. Urgent needs in technological support require developing new diagnostic platforms that can either detect cancer at an early stage, where cancer cells may be more difficult to detect, or monitor tumor progression.

SUMMARY OF THE INVENTION

The present invention provides a method for obtaining gene expression profiles of individual CTCs for cancer diagnosis and/or prognosis. The invention also provides an integrated CTC platform for implementing the method. The present invention provides capability to clearly distinguish between cells of cancer and non-cancer origins, with higher sensitivity and specificity than that of the state-of-the-art immunostaining classification technique of CTC identification.

In one aspect, the invention provides a method for identification of circulating tumor cells (CTCs) in a blood sample using magnetic enrichment and a nanowell assay. The CTCs are magnetically labeled with cancer cell markers conjugated to magnetic nanoparticles. For example, the cancer cell markers may be conjugated to magnetic nanoparticles through epithelial cell adhesion molecule antibodies, HER2 antibodies, or other antibodies against cancer surface markers. The magnetically labeled CTCs are then separated by passing the blood sample through a magnetic sifter during application of an external magnetic field. The separated magnetically labeled CTCs are then collected to produce enriched CTCs, which are then loaded into a microfluidic single-cell molecular assay comprising an array of 25,600 or more nanowells, where each of the nanowells is adapted to contain at most a single one of the CTCs. Using the microfluidic single-cell molecular assay and multiple fluorescent gene markers, multiple simultaneous multiple-color multiplexed gene expression of the CTCs is performed, preferably using RT-PCR, where there is concurrent expression of two or more genes. The array of nanowells is imaged using fluorescence signal acquisition from individual nanowells, producing images of the array of nanowells. The images are analyzed using a signal processor to identify CTCs based on the concurrent expression of two or more genes. Preferably, the image analysis identifies CTCs using an outlier identification method such that a nanowell is classified as positive if its expression of two or more genes is greater than 3 standard deviations away from a distribution expected for empty wells.

The method may include one or more additional steps to further enhance sensitivity, such as double sifting of the magnetically labeled CTCs, performing red blood cell lysis, performing DNase treatment, or performing CD45 staining for leukocyte exclusion.

The method may include performing multiple simultaneous multiple-color multiplexed genotyping of the CTCs for mutational detection using the microfluidic single-cell molecular assay and multiple fluorescent gene markers. The method may include performing multiple simultaneous multiple-color multiplexed genotyping of the CTCs where non-CTCs are identified based on the intensity of gene expression of one or more genes.

These and other aspects of the invention are set forth in more detail in the following detailed description and associated drawing figures.

DETAILED DESCRIPTION

Embodiments of the present invention include integrated nanotechnology methods and devices for biomedical analysis that enable the molecular profiling of tumor-derived cells from peripheral blood samples.

Figure 1:
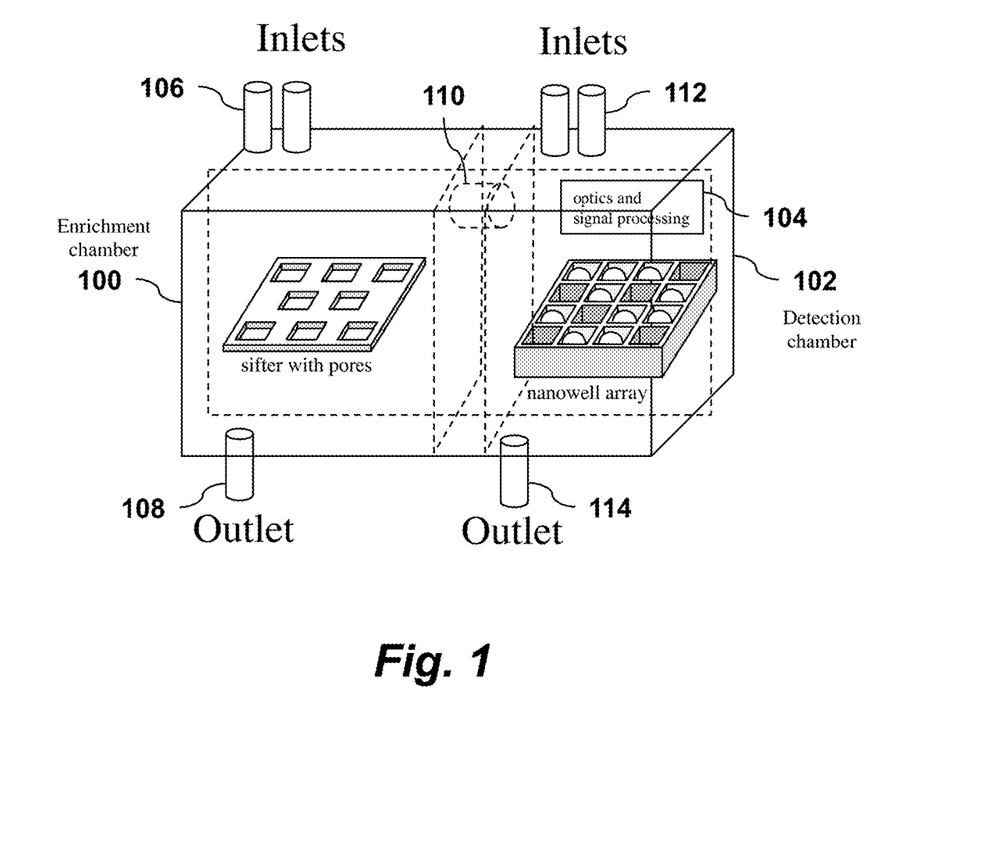
FIG. 1 illustrates a device integrating a magnetic enrichment chamber and detection chamber for implementing a method for identification of circulating tumor cells (CTCs) in a blood sample, according to an embodiment of the invention.

In one embodiment of the invention, shown in FIG. 1, a device provides a technological integration of a magnetic enrichment chamber 100 and a detection chamber 102.

The magnetic enrichment chamber 100 is a magnetic rare cell separation platform for isolating and enriching rare cells from peripheral blood samples. Preferably, it includes a magnetic sifter (MagSifter™) device. This magnetic sifter offers increased capture efficiency at high flow rates due to extreme field gradients at the pore edges, high throughput due to the density of pores (~200 pores/mm$^2$), scalability via standard lithographic fabrication, and harvesting of viable cells. The inlets 106 allow injection of blood samples or reagents, while unwanted cells and blood components as well as wastes are collected at outlet 108. The eluted CTCs are passed to detection chamber through the connecting channel 110.

The detection chamber 102 is a multiplexed microfluidic device that performs single-cell RT-PCR of the isolated rare cells using a nanowell array assay. This microfluidic single-cell molecular assay performs multiple simultaneous gene expression analysis and genotyping from single cells. Specific gene markers are selected for (a) early diagnosis of cancer, and (b) genotyping, e.g. mutational analysis, which may inform cancer therapy selection and monitoring. The inlets 112 allow injection of lysis buffer and RT-PCR reagents, and the excess reagents and wastes are passed to outlet 114.

The detection chamber 102 includes a massive multiplexed array of nanowells that enables single-cell RT-PCR on chip of rare cells that have been isolated by a magnetic sifter device from whole blood samples. In one embodiment, a standard optical and signal processing module 104 is used to interrogate the Nanowell using conventional fluorescence microscopy to detect a candidate panel of genes on CTCs that are relevant for cancer detection or therapy monitoring. The nanowell is low-cost (PDMS-based) and scalable (from currently 25 $k$ to more than 100 k nanowells). The nanowell-based RT-PCR has sufficient efficiency for the discrimination of cell sub-populations. One to thousands of cells that have been enriched by the Magnetic sifter cell sorters can be loaded into the nanowell by direct pipetting and centrifugation (e.g., 3,000 rpm for 10 min.) or by automated fluidics techniques. The nanowell dimensions are engineered such that single cells settle into different wells, each of which serves as a miniaturized RT-PCR reaction chamber for mRNA analysis. For example, in one implementation, each of the 25,600 nanowell compartments are 20×20×50 μm$^3$, with 20-pL volumes that are 10$^6$ times smaller than those of typical PCR assays, thereby enabling higher sensitivity from higher mRNA concentrations.

In another embodiment, a four-color-based single-cell gene expression assay is used to classify each captured cell from a patient sample. Isolation and enrichment of CTCs from the magnetic sifter is assayed by the nanowell for massive single-cell targeted gene expression analysis. This is typically achieved within 8 hours from patient blood draw to data analysis.

Various techniques may be used to improve integration of these two technological platforms for better mutual compatibility and to enable high-sensitivity and high-specificity molecular profiling of tumor-derived cells. For example, these techniques may include double sifting, red blood cell lysis, deoxyribonuclease (DNase) treatment, and CD45 staining for leukocyte exclusion. For example, double sifting can be performed by collecting the eluted cells at the outlet 108 and re-sifting in chamber 100 before passing the final eluted cells to the detection chamber 102.

A method for identification of circulating tumor cells (CTCs) in a blood sample using magnetic enrichment and a nanowell assay will now be described in more detail. The method effectively enriches rare cells via a magnetic sifting technology using magnetic nanoparticles to tag CTCs in conjunction with magnetic filtration to enable high-throughput enrichment with release capability. For subsequent characterization of the enriched cells, a robust microwell-based assay was designed to circumvent experimental errors associated with ensemble measurements through detection of mRNA transcripts directly from single CTCs (using one-step RT-PCR). These massive single-cell arrays are able to isolate up to thousands of single lung cancer cells to measure gene expression and to observe the translational kinetics of single cancer cells.

As an initial step, CTCs in a whole blood sample (e.g., 2 mL) are magnetically labeled with cancer cell markers conjugated to magnetic nanoparticles. For example, the cancer cell markers may be epithelial cell-adhesion molecules (EpCAM), Human Epidermal Growth Factor Receptor 2 (HER2) antigens, or other cancer surface markers. In one embodiment, streptavidin coated 150-nm iron oxide magnetic nanoparticles (R&D, MAG999) are conjugated to biotinylated anti-EpCAM antibodies (BioLegend) which will in turn couple to the EpCAM markers on the cancer cells.

Figure 2A:
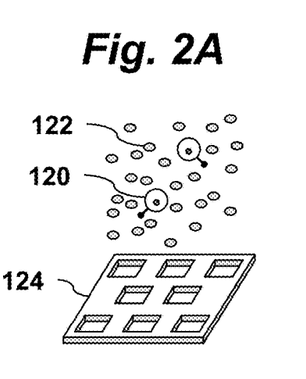
FIGS. 2A, 2B, 2C illustrate three steps in a technique for separating magnetically labeled CTCs from other cells using a magnetic sifter, according to an embodiment of the invention.
Figure 2B:
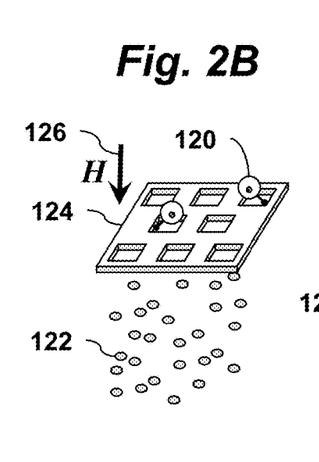
Figure 2C:
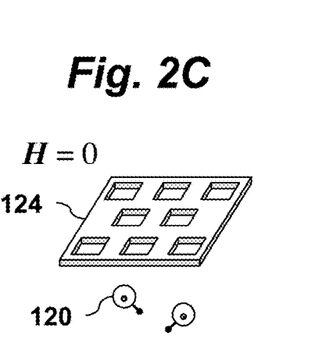

The magnetically labeled CTCs are then separated by pumping the blood sample through pores of a magnetic sifter during application of an external magnetic field. FIG. 2A shows labeled CTCs 120 and other cells 122 before passing through a sifter 124. FIG. 2B shows the labeled CTCs 120 attached to the edges of the pores of the sifter 124 during application of a magnetic field H, while the other (unlabeled) cells 122 pass freely through the pores. This separates the CTCs from the other cells. FIG. 2C shows the labeled CTCs 120 released from the edges of the pores of the sifter 124 after the magnetic field H is turned off, allowing the separated CTCs 120 to be released and collected for downstream analysis.

Figure 2D:
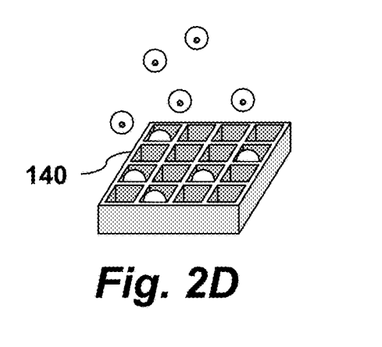
FIG. 2D illustrates a step of seeding a nanowell array with CTCs, according to an embodiment of the invention.

After the separated magnetically labeled CTCs are collected to produce enriched CTCs, they are then loaded into a microfluidic single-cell molecular assay comprising an array 140 of 25,600 or more nanowells, as shown in FIG. 2D. Each of the nanowells in the array 140 is adapted to contain only a single one of the CTCs or to remain empty.

For example, in one implementation, after cell collection, the effluent from the device is subsequently treated with red blood cell lysis buffer (ammonium chloride-based) to further remove RBC contamination, and also treated with DNase to remove all possible DNA fragments of non-CTC origin. Optionally, the effluent may be sent through the magnetic sifter again in order to increase purity.

Figure 2E:
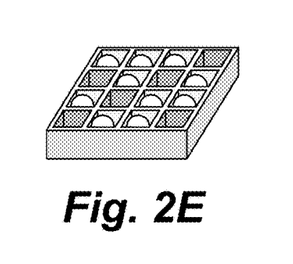
FIG. 2E illustrates a step of performing simultaneous multiple-color multiplexed gene expression of the CTCs in the nanowell array, according to an embodiment of the invention.

All effluent is then loaded on top of a nanowell device by centrifugation, and cellular contents are seeded into individual nanowell compartments. Preferably, fluorescence microscope images of the entire nanowell array are acquired for identification and exclusion of wells containing WBCs by CD45 signal. After drying (e.g., 70° C. for 10 min) to fix seeded cells into the wells and to completely deactivate the DNase, single-cell RT-PCR master mix is applied to the nanowells, which are then sealed with a small piece of adhesive PCR sealant film (Bio-Rad). In one implementation, the RT-PCR master mix consisted of 2× reaction mix (CellsDirect™ One-Step qRT-PCR, Life Technologies), polymerases (SuperScript® III RT/Platinum® Taq Mix), TaqMan® probes (Life Technologies; Bio-Rad, Hercules, Calif.) for targeting specific genes, and DEPC-treated water After the seeding and reagent application, gene expression of the CTCs in each individual nanowell is performed. More specifically, the microfluidic single-cell molecular assay and multiple fluorescent gene markers are used to perform multiple simultaneous multiple-color multiplexed gene expression of the CTCs. This is preferably performed using RT-PCR, where there is concurrent expression of two or more genes in each individual nanowell, as shown in FIG. 2E. For example, in one implementation, the nanowell chip is placed into a thermocycler (PTC-200, Peltier Thermal Cycler, Bio-Rad) for gene expression via PCR amplification using the following cycle parameters: for the first thermal cycler step, cell lysis and subsequent reverse transcription, the array was incubated at 50° C. for 45 min. This was followed by 10 cycles of 60 s at 95° C. for denaturation and 90 s at 65° C. for an annealing and extension step. Amplification commenced after with 35 cycles of 60 s at 90° C. and 90 s at 60° C. For fully automatic work flow, a heating element (not shown) is integrated in the detection chamber to facilitate thermal cycling.

The array of nanowells is imaged using fluorescence microscope signal acquisition from individual nanowells, producing images of the array of nanowells.

Figure 2F:
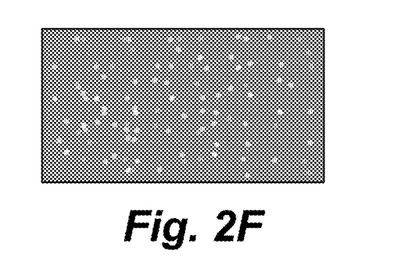
FIG. 2F shows an image of fluorescence signal acquisition from individual nanowells where cMET is expressed in particular individual nanowells, according to an embodiment of the invention.
Figure 2G:
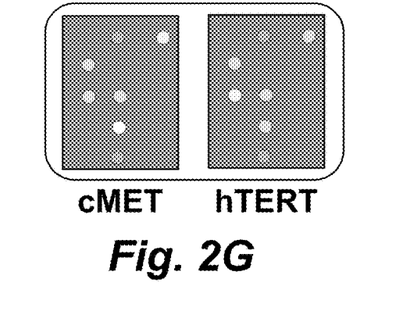
FIG. 2G shows an image of fluorescence signal acquisition from individual nanowells where hTERT is expressed in particular individual nanowells, according to an embodiment of the invention.

For example, FIG. 2F shows signal acquisition from individual nanowells where cMET is expressed in particular individual nanowells, and FIG. 2G shows signal acquisition from individual nanowells where hTERT is expressed in particular individual nanowells. Single CTCs displaying hTERT only, cMet only, and both were evident upon imaging. Because each nanowell contains at most one CTC, the image signals from the individual nanowells allow identification of CTCs on an individual cell basis.

The images are analyzed using a signal processor to identify CTCs based on the concurrent expression of two or more genes. The individual nanowell fluorescence signals are analyzed for identification of tumor-derived cellular material based on double positive (cMET+ and hTERT+) gene expression. Preferably, the image analysis identifies CTCs using an outlier identification method such that a nanowell is classified as positive if its expression of two or more genes is greater than 3 standard deviations away from a distribution expected for empty nanowells. This outlier identification method capitalizes on the fact that the majority of the wells are empty due to the rarity of the putative CTCs. Assuming a Gaussian distribution for the empty well signals, we define wells as being positive if they are greater than 3 standard deviations away from the distribution expected for these empty wells.

Since each Nanowell array contains 25,600 wells and the CTC population from 2 mL of blood is expected to be no more than 2,000 cells, each individual well has a 99.7% chance of containing either a single cell or no cell, according to the Poisson distribution, and only a 0.3% chance of containing two or more cells, thereby representing a high-throughput method of analyzing "single" cells.

The nanowell assay provides significant advantages over conventional bulk assay. In a bulk assay (RT-PCR of either from all cells from cell culture or all the cells captured by magnetic separation), the background signal is inevitable and a serious limiting factor (contributing to false positives). In a nanowell assay, the vast majority of nanowells which contribute just background signal are automatically excluded, greatly boosting the biological signal to noise ratio when we process the fluorescent images.

In another embodiment, four-color gene expression from a single nanowell can be achieved as follows. H1650 cells are spiked into healthy whole blood samples (mimicking a patient blood condition) and processed through the previously described workflow. Four genes are selected for identification of CTCs:

hTERT—human telomerase reverse transcriptase;
cMET—hepatocyte growth factor receptor, a proto-oncogene) and assessment of metastatic capability;
VIM—Vimentin, an Epithelial-to-Mesenchymal (EMT) marker;
ALDH1A3—aldehyde dehydrogenase.

Four fluorophores are used for multiplex single-cell gene expression profiling, where primer-probe sets have four discrete excitation-emission spectra that can be resolved by fluorescence microscopy. Probes with 4 different fluorophores and minimal spectral overlap are selected for simultaneous 4-plex gene expression capability. The 4 fluorophores, FAM, HEX, Texas Red, and Cy5, have excitation and emission peaks of 492 and 517 nm, 530 and 556 nm, 596 and 615 nm, and 650 and 670 nm, respectively. Primer-probe assays were obtained commercially: TERT (Life Technologies), MET (Life Technologies), VIM (Bio-Rad), and ALDH (Bio-Rad). The 4-plex RT-PCR process is optimized on conventional bulk assay in a CFX96 Touch™ Real-Time PCR Detection System (Bio-Rad).

Figure 3A:
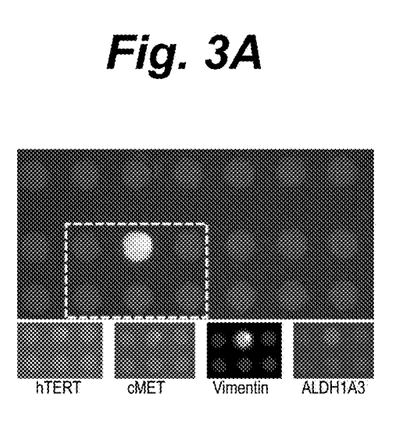
FIG. 3A shows the results of four-color gene expression, where white blood cells only express VIM significantly, according to an embodiment of the invention.
Figure 3B:
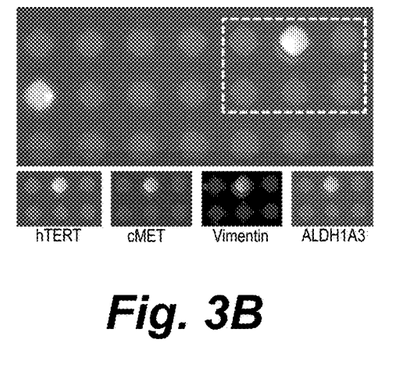
FIG. 3B shows the results of four-color gene expression, where H1650 cells fully express hTERT, cMET, and VIM, and partially express ALDH1A3, according to an embodiment of the invention.
Figure 3C:
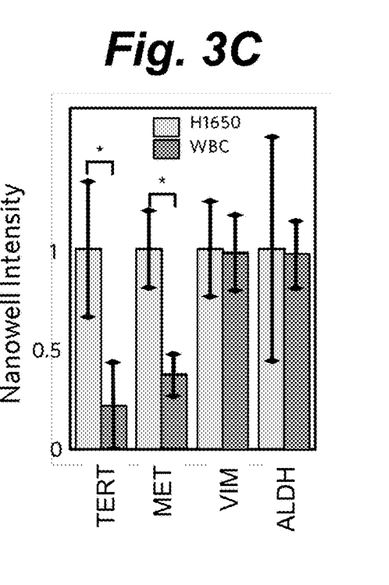
FIG. 3C is a graph of an ensemble analysis showing the clear discernment of TERT/MET expression levels in WBC and H1650 cells, according to an embodiment of the invention.

FIGS. 3A-C show the results of four-color gene expression from a single nanowell. FIG. 3A shows an image of a nanowell array, where white blood cells only express VIM significantly. FIG. 3B shows an image of a nanowell array, where H1650 cells fully express hTERT, cMET, and VIM, and partially express ALDH1A3 (in contrast to white blood cells, which only express VIM significantly). FIG. 3C is a graph of an ensemble analysis showing the clear discernment of TERT/MET expression levels in WBC and H1650 cells.

The 4-plex assay developed to analyze CTC gene expression can be correlated with patient diagnosis and CT and PET-CT imaging data.

The demonstrated number multiplexed gene markers is limited only by the fluorescent dye colors developed.

In other embodiments, multiplexed RT-PCR may be performed in a nanowell array with other labels like Raman labels, which may allow deep multiplexing well beyond four gene markers. For example, Raman labels based on composite organic-inorganic nanoparticles (COINs) are capable of multiplexed labeling well beyond four unique optical signatures.

In another embodiment, genotyping of cells can also be performed. For example, two NSCLC cell lines may be used to represent different gene expression patterns according to their Epidermal Growth Factor Receptor (EGFR) Exon 19 deletion mutational status. Bulk PCR analysis shows that HCC827 has measured signal for only the EGFR Exon 19 deletion mutation, while H661 exhibits measured signal for only the EGFR wild-type gene. The same two cell lines (HCC827 and H661) were then spiked into a nanowell device, and the bulk PCR results can be directly translated to the corresponding nanowell signal. HCC827 shows only the green signal (denoting FAM dye resulting from EGFR Exon 19 deletion mutation amplification), while H661 exhibits only the orange signal (denoting HEX dye resulting from EGFR wild-type amplification). These results can be applied to patient samples in order to perform genotyping that can inform therapy selection and monitoring in clinical settings.

Figure 4A:
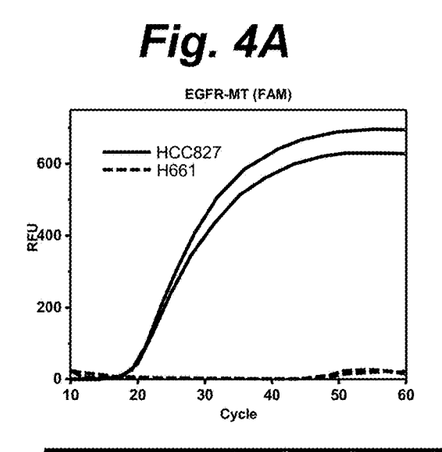
FIGS. 4A, 4B show the bulk RT-PCR signal intensity versus the thermal cycle number for two cell lines (HCC827 and H661) used to represent different gene expression patterns according to their Epidermal Growth Factor Receptor (EGFR) Exon 19 deletion mutational status, according to an embodiment of the invention.
Figure 4B:
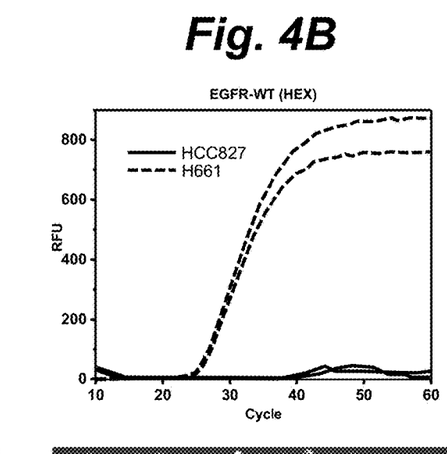
Figure 4C:
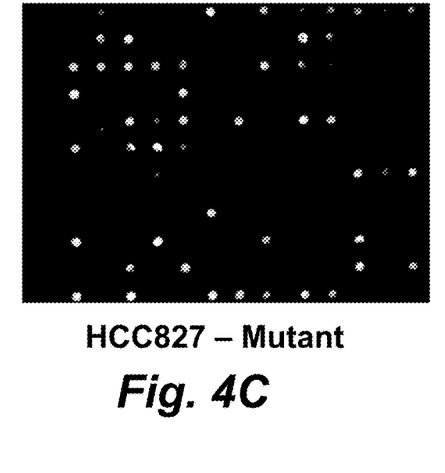
FIGS. 4C, 4D are nanowell images of the same two cell lines (HCC827 and H661) spiked into a nanowell device, according to an embodiment of the invention.
Figure 4D:
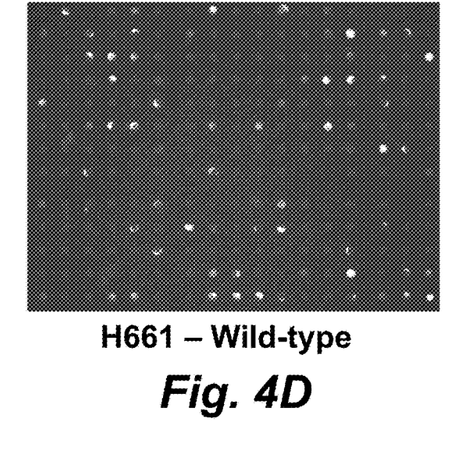

FIGS. 4A-D compare genotyping in bulk vs. nanowell. In the bulk, FIGS. 4A-B show the bulk RT-PCR signal intensity versus the thermal cycle number for two cell lines used to represent different gene expression patterns according to their Epidermal Growth Factor Receptor (EGFR) Exon 19 deletion mutational status. Bulk PCR analysis shows that HCC827 has measured signal for only the EGFR Exon 19 deletion mutation, while H661 exhibits measured signal for only the EGFR wild-type gene. FIGS. 4C-D are nanowell images of the same two cell lines (HCC827 and H661) spiked into a nanowell device, and the results from FIGS. 4A-B can be directly translated to the corresponding Nanowell signal. HCC827 shows only the green signal (denoting FAM dye resulting from EGFR Exon 19 deletion mutation amplification), while H661 exhibits only the orange signal (denoting HEX dye resulting from EGFR wild-type amplification). These results can be applied to patient samples in order to perform genotyping, e.g., mutational detection, that can inform therapy selection and monitoring in clinical settings, according to the current invention.

Figure 5:
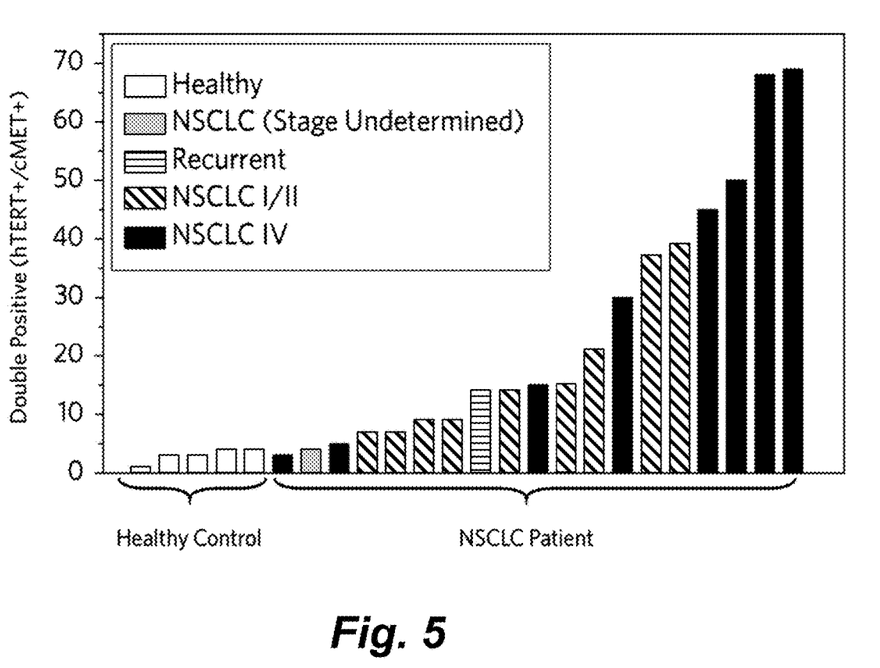
FIG. 5 is a graph comparing the number of nanowells with double positive (hTERT+/cMET+) expression of five healthy control individuals with a NSCLC patient (stage undetermined), a recurrent NSCLC patient, multiple NSCLC stage I/II patients, and multiple NSCLC stage IV patients, according to an embodiment of the invention.

FIG. 5 is a graph comparing the number of nanowells with double positive (hTERT+/cMET+) expression of five healthy control individuals with a NSCLC patient (stage undetermined), a recurrent NSCLC patient, multiple NSCLC stage I/II patients, and multiple NSCLC stage IV patients. The cancer patients have generally greater number of putative CTCs than healthy controls, indicating that our methodology is capable of discriminating cancer patients from health individuals.

In some embodiments, an optimized single-cell RT-PCR procedure may be used when performing simultaneous molecular profiling of individual cells with four genes. Specifically, the selection of gene markers for early diagnosis and clinical assessment of cancer includes human telomerase reverse transcriptase (hTERT), hepatocyte growth factor receptor (cMET or HGFR, a proto-oncogene), Vimentin (VIM, an Epithelial-to-Mesenchymal (EMT) marker), and aldehyde dehydrogenase (ALDH1A3). The selection of gene markers for genotyping may also include hepatocyte growth factor receptor (cMET or HGFR, a proto-oncogene), Epidermal Growth Factor Receptor (EGFR) Exon 19 deletion mutation, EGFR wild-type, programmed death-ligand 1 (PD-L1).

The technology described in the embodiments above are intended to be illustrative examples. Variations and extensions of these embodiments are envisioned as within the scope of the invention. For example, multiple capture antibodies may be used to enable comprehensive enrichment of an entire population of heterogeneous CTCs. Although the embodiments are described using EpCAM enrichment, the nanowell assay is highly sensitive and specific to tumor-derived cells neglected by immunocytochemistry. Moreover, the magnetic sifter can be generalized to accommodate multiple cell capture antibodies instead of, or in conjunction with, EpCAM. This would provide detection of other cancers that shed CTCs (e.g. human epidermal growth factor receptor (HER2) for breast cancer, neuron-glial antigen 2 (NG2) for melanoma, and carbonic anhydrase IX (CAIX) for renal cell carcinoma) and to EpCAM-low and EpCAM-negative populations. In addition, the invention is not limited to 4 fluorophores for multiplex single-cell gene expression profiling. As additional primer-probe sets become commercially available, additional or alternative ones may be used as well. Moreover, further modifications, including laser excitation, sharper band-pass filters, and narrower-emission hydrolysis probes, may extend the platform's multiplex capability to accommodate 12 or more genes. Such expansion allows comprehensive mutational profiling to develop along with clinical advances to capture a comprehensive panel of relevant "actionable" mutations for therapy selection and disease monitoring.

In conclusion, embodiments of the invention provide a massively parallel, multigene profiling nano-platform and method to analyze hundreds of single CTCs. It features a magnetic sifter for high-efficiency CTC enrichment from blood and a single-cell nanowell array for CTC mutation profiling using modular gene panels. This approach to interrogate individual CTCs has unprecedented sensitivity. To our knowledge, this is the first demonstration of a high-throughput, multiplexed strategy for single-cell gene mutation profiling of CTCs to provide minimally invasive cancer therapy prediction and disease monitoring.

The invention claimed is:

1. A method for identification of circulating tumor cells (CTCs), the method comprising:
    magnetically labeling the CTCs in a blood sample with cancer cell markers conjugated to magnetic nanoparticles;
    separating the magnetically labeled CTCs by passing the blood sample through a magnetic sifter during application of an external magnetic field;
    collecting the separated magnetically labeled CTCs to produce enriched CTCs;
    loading the enriched CTCs into a microfluidic single-cell molecular assay comprising an array of 25,600 or more nanowells, where each of the nanowells is adapted to contain at most a single one of the CTCs;
    performing multiple simultaneous multiple-color multiplexed gene expression analysis of the CTCs using the microfluidic single-cell molecular assay and multiple fluorescent gene markers;
    imaging the array of nanowells using fluorescence signal acquisition from individual nanowells, producing images of the array of nanowells;
    analyzing the images using a signal processor to identify CTCs based on the concurrent expression of two or more genes.

2. The method of claim 1 further comprising:
    performing multiple simultaneous multiple-color multiplexed genotyping of the CTCs for mutational detection using the microfluidic single-cell molecular assay and multiple fluorescent gene markers.

3. The method of claim 1 further comprising:
performing multiple simultaneous multiple-color multiplexed genotyping of the CTCs wherein non-CTCs are identified based on the intensity of gene expression of one or more genes.

4. The method of claim 1 wherein the microfluidic single-cell molecular assay is performed by RT-PCR.

5. The method of claim 1 wherein the cancer cell markers are conjugated to magnetic nanoparticles through one or more molecules selected from epithelial cell adhesion molecule antibodies, HER2 antibodies, and other antibodies against cancer surface markers.

6. The method of claim 1 further comprising:
double sifting of the magnetically labeled CTCs.

7. The method of claim 1 wherein analyzing the images using a signal processor to identify CTCs comprises using an outlier identification method such that a nanowell is classified as positive if its expression of two or more genes is greater than 3 standard deviations away from a distribution expected for empty wells.

* * * * *